United States Patent
Maldonado

(10) Patent No.: US 9,314,084 B2
(45) Date of Patent: Apr. 19, 2016

(54) CLANDESTINE LOTION DISPENSING APPARATUS

(71) Applicant: Lisa Maldonado, Topeka, KS (US)

(72) Inventor: Lisa Maldonado, Topeka, KS (US)

( * ) Notice: Subject to any disclaimer, the term of this patent is extended or adjusted under 35 U.S.C. 154(b) by 275 days.

(21) Appl. No.: 14/021,385

(22) Filed: Sep. 9, 2013

(65) Prior Publication Data

US 2015/0071697 A1  Mar. 12, 2015

(51) Int. Cl.
*A45D 34/04* (2006.01)
*A61M 35/00* (2006.01)
*A45D 34/00* (2006.01)
*A46B 11/00* (2006.01)

(52) U.S. Cl.
CPC ............... *A45D 34/04* (2013.01); *A61M 35/00* (2013.01); *A45D 2034/002* (2013.01); *A45D 2034/007* (2013.01); *A45D 2200/1009* (2013.01); *A45D 2200/1081* (2013.01); *A46B 11/00* (2013.01)

(58) Field of Classification Search
CPC .............. A45D 2200/1009; A45D 2200/1081; A45D 34/04; A61M 35/00
USPC .......... 401/195; 15/118; 108/38–40; 49/246–260
See application file for complete search history.

(56) References Cited

U.S. PATENT DOCUMENTS

| | | | |
|---|---|---|---|
| 3,078,484 A * | 2/1963 | Briggs | A47K 7/043 |
| | | | 15/21.1 |
| 4,039,104 A | 8/1977 | Mijares, Jr. et al. | |
| 5,452,825 A | 9/1995 | Comstock et al. | |
| 5,490,302 A | 2/1996 | Dion | |
| 5,573,342 A | 11/1996 | Patalano | |
| 5,628,083 A | 5/1997 | Hayes | |
| 6,092,254 A * | 7/2000 | Kay | A45D 40/26 |
| | | | 15/105 |
| 6,546,290 B1 | 4/2003 | Shloznikov | |
| 7,422,575 B2 | 9/2008 | Dallabetta | |
| 8,272,801 B2 | 9/2012 | Linzell | |
| 2002/0054782 A1 | 5/2002 | Andreas | |
| 2009/0083923 A1 | 4/2009 | Kilian | |
| 2013/0066245 A1 | 3/2013 | Dagan | |

* cited by examiner

*Primary Examiner* — Mark A Laurenzi
*Assistant Examiner* — Thomas M Abebe
(74) *Attorney, Agent, or Firm* — Dale J. Ream

(57) ABSTRACT

A dispensing apparatus includes a display panel having a back surface and a dispensing device coupled to the back surface of the display panel. The dispensing display device may include a medicament pad configured to dispense medicine, lotion, or the like. The dispensing apparatus includes a display housing. The display panel is selectively coupled to the display housing so as to define a void between the display panel and the display housing when coupled thereto. The dispensing device is selectively positioned at a first configuration in which the dispensing device is situated within the void and a second configuration in which the dispensing device is situated outside the void. The display housing may include one or more channels and the display panel may include one or more bosses such that display panel may be reversed in orientation by slidable operation of respective bosses in respective channels.

16 Claims, 6 Drawing Sheets

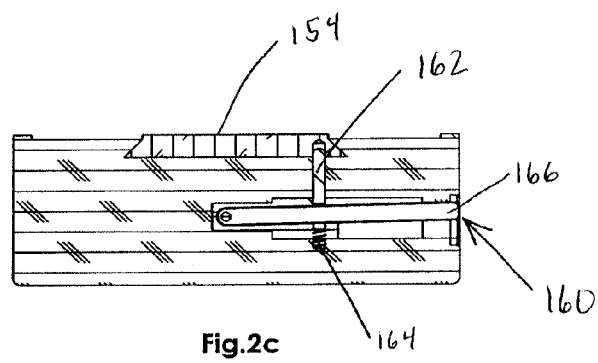
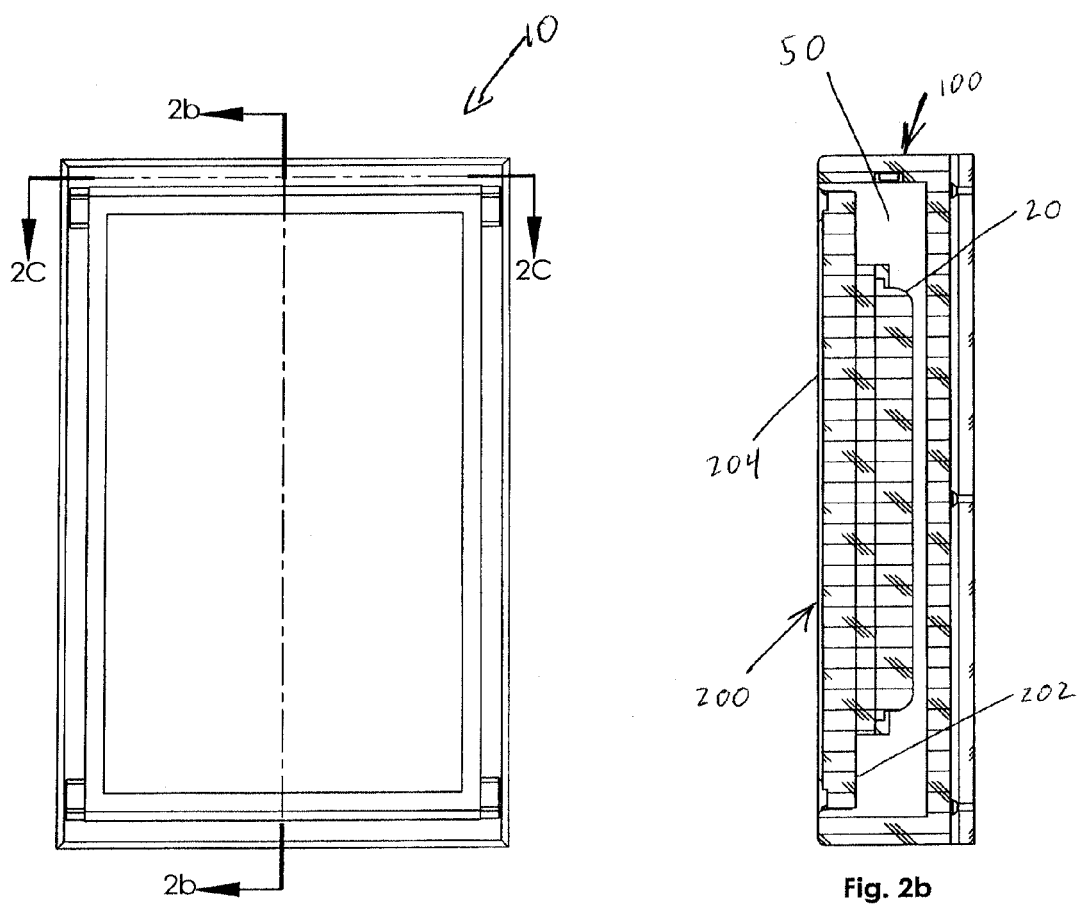

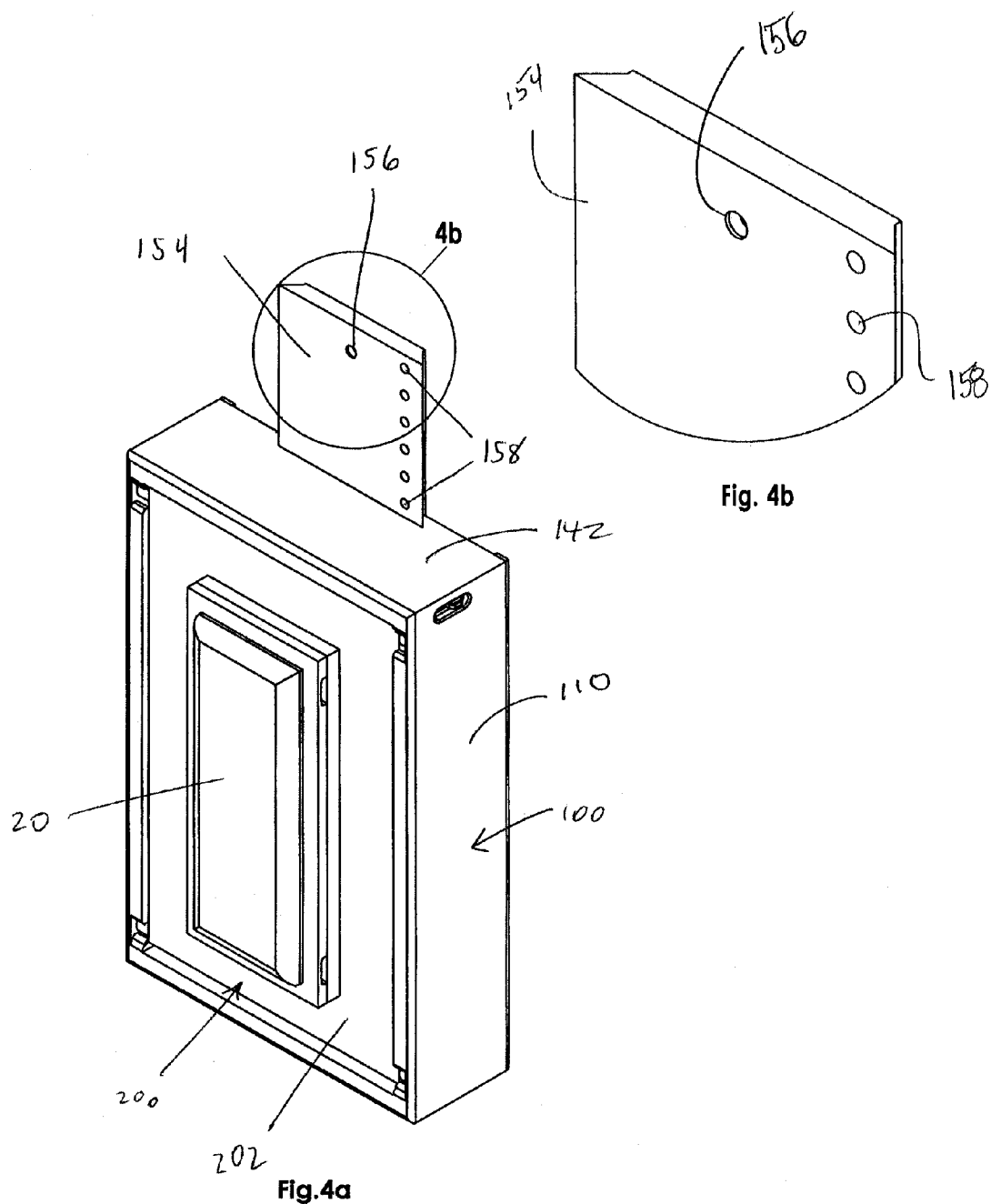

CLANDESTINE LOTION DISPENSING APPARATUS

BACKGROUND OF THE INVENTION

This invention relates generally to lotion dispensing devices and, more particularly, to a clandestine lotion dispensing apparatus that reveals a dispensing device in a use configuration and conceals the dispensing device in a non-use configuration.

It is well-known and appreciated that it is difficult to apply lotion to one's own back. Many handheld and mounted devices have been developed to help resolve this problem. Handheld devices are easy to conceal when not in use, but their manual dexterity requirements often make them impractical or inconvenient to use. Mounted devices, on the other hand, are often mounted in a shower and are easier to use, but are unsightly when mounted anywhere other than a bathroom. Although assumably effective for their intended purposes, the existing devices and proposals do not present a device that is both convenient to use and convenient to conceal in a location other than a bathroom.

Therefore, it would be desirable to have a clandestine lotion dispensing apparatus that is both easy to use and easy to conceal when mounted and not in use. Further, it would be desirable to have a lotion dispensing apparatus that is vertically adjustable to be useful for use by persons of different height.

SUMMARY OF THE INVENTION

A dispensing apparatus according to the present invention includes a display housing, a display panel having a back surface, and a dispensing device coupled to the back surface of the display panel. The dispensing device may be a medicament pad configured to dispense medicine, lotion, or the like. The display panel is selectively coupled to the display housing so as to define a void between the display panel and the display housing when coupled thereto. The dispensing device is selectively positioned at a first configuration in which the dispensing device is situated within the void and a second configuration in which the dispensing device is situated outside the void. The display housing may include one or more channels and the display panel may include one or more bosses such that the display panel may be reversed in orientation by slidable operation of respective bosses in respective channels.

Therefore, a general object of this invention is to provide a clandestine lotion dispensing apparatus in which a dispensing pad for dispensing lotion is displayed when desired for use and hidden from view when not needed.

Another object of this invention is to provide a clandestine lotion dispensing apparatus, as aforesaid, having a display panel having the dispensing pad mounted to one side of the display panel and a neutral article on a reverse side of the display panel, the display panel being rotatable between the two sides.

Still another object of this invention is to provide a clandestine lotion dispensing apparatus, as aforesaid, in which an entire display housing and display panel may be mounted to a wall and are vertically adjustable to a user selected height.

Yet another object of this invention is to provide a clandestine lotion dispensing apparatus, as aforesaid, in which the dispensing device is removable from the display panel, such as for refill, replacement, or to be used apart from the display housing.

A further object of this invention is to provide a clandestine lotion dispensing apparatus, as aforesaid, that appears to be a normal household wall display when the dispensing apparatus is at a hidden configuration.

A still further object of this invention is to provide a clandestine lotion dispensing apparatus, as aforesaid, that is easy to use by persons of different heights.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2a is a front view of the dispensing apparatus as in FIG. 1a;

FIG. 2b is a sectional view taken along line 2b-2b of FIG. 2a;

FIG. 2c is a sectional view taken along line 2c-2c of FIG. 2a;

FIG. 4a is a perspective view of the dispensing apparatus, as in FIG. 1a, showing a wall mounting member protruding from the top of a display housing;

FIG. 4b is an isolated view on an enlarged scale taken from FIG. 4a;

FIG. 6b is a side view of the dispensing apparatus as in FIG. 6a.

DESCRIPTION OF THE PREFERRED EMBODIMENT

Figure 1C:
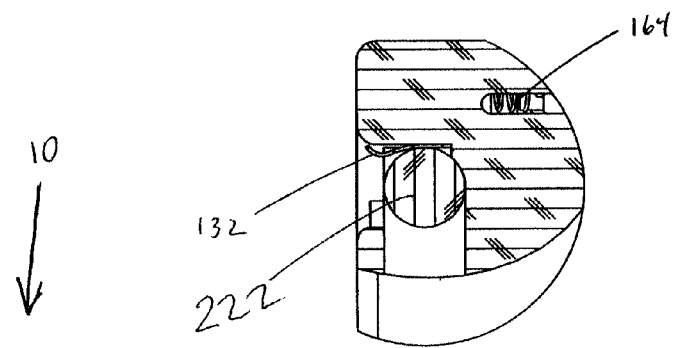
FIG. 1c is an isolated view on an enlarged scale taken from FIG. 1b.
Figure 1A:
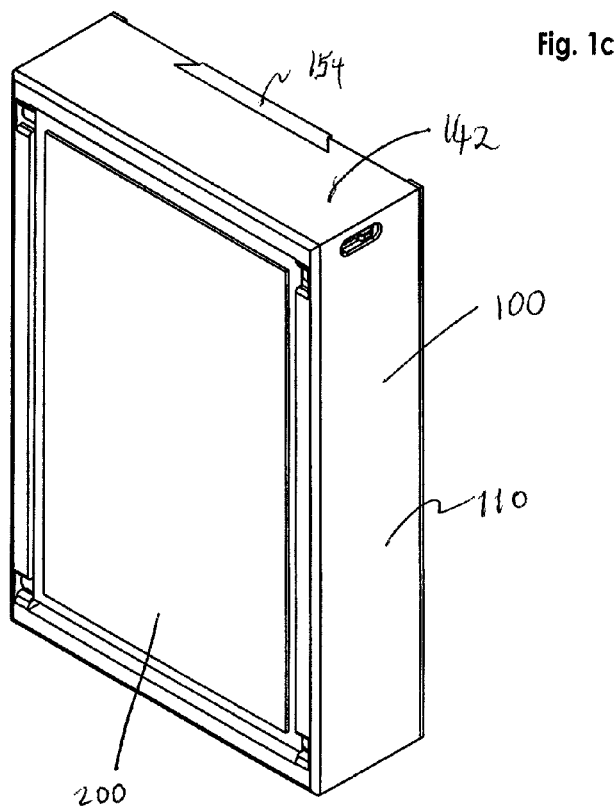
FIG. 1a is a perspective view of a clandestine lotion dispensing apparatus according to a preferred embodiment of the present invention.

A clandestine lotion dispensing apparatus according to a preferred embodiment of the present invention will now be described with reference to FIGS. 1a to 5d of the accompanying drawings. The dispensing apparatus 10 includes a display housing 100, a display panel 200 having a back surface 202, and a dispensing device 20 coupled to the back surface 202 of the display panel 200.

Figure 1B:
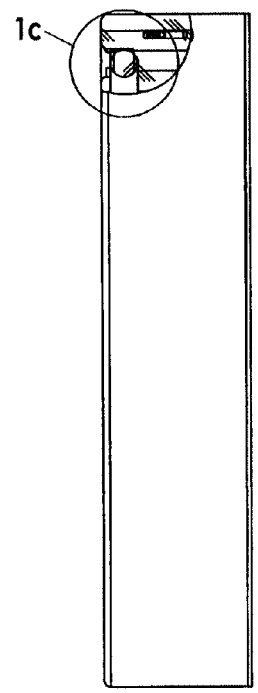
FIG. 1b is a side elevation view of the dispensing apparatus, as in FIG. 1a, shown with the top left corner cut away revealing a portion of the internal structure.

The display panel 200 is selectively coupled to the display housing 100 so as to define a void 50 between the display panel 200 and the display housing 100. The dispensing device 20 is situated within the void 50 when the display panel 200 is selectively coupled to the display housing 100 in a first configuration (FIG. 2b). The dispensing device 20 is situated outside the void 50 when the display panel 200 is selectively coupled to the display housing 100 in a second configuration (FIG. 1). In one embodiment, the dispensing device 20 may be a medicament applicator pad configured to selectively dispense a medicated lotion. Similarly, the applicator pad may dispense a skin softening lotion or even tanning lotion. In user, a person may rub his back against the dispensing pad and, as a result, spread lotion over his back.

In another embodiment, the dispensing device 20 may be removably coupled to the back surface 202 of the display panel 200. More particularly, the dispensing device 20 may be attached in a snap-fit or friction-fit arrangement or with a fastener as would be understood by one of ordinary skill in the art. It is advantageous for the dispensing device 20 to be removable in that it may be replaced or replenished by a user as needed.

The display panel 200 may have a generally planar configuration with a front surface 204. An article of manufacture 40 may be coupled to the front surface 204 of the display panel 200. The article of manufacture 40 may be a picture frame, a mirror, a towel bar, a clock, a sconce, or any similar article of manufacture 40. When the display panel 200 is selectively coupled to the display housing 100 in the first configuration, the article of manufacture 40 is situated outside the void 50. When the display panel 200 is selectively coupled to the display housing 100 in the second configuration, the article of manufacture 40 is situated within the void 50 and is, therefore, concealed.

In the preferred embodiment, the display housing 100 includes a pair of opposed upstanding side panels 110 each having an upper end 112 and a lower end 114, opposing upper and lower panels 142, 144 extending between respective upper and lower ends 112, 114, and a back panel 140 extending between respective side panels 110 and respective upper and lower panels 142, 144 so as to define an interior area 150.

In the preferred embodiment, each side panel 110 includes an inner surface 116 that defines a channel 120 and opposed slots 130. Each respective channel 120 may extend substantially between respective upper and lower ends 112, 114 of each respective side panel 110. The opposed slots 130 may be located adjacent to respective upper and lower ends 112, 114 of the respective side panels 110. Respective slots 130 may be in communication with, and configured as entrances and exits to, respective channels 120. In one alternative embodiment, the slots 130 are not required. In another alternative embodiment, only one channel 120 is required. Respective slots 130 and respective channels 120 enable the display panel 200 to move between first and second configurations as will be described in more details below.

Figure 3:
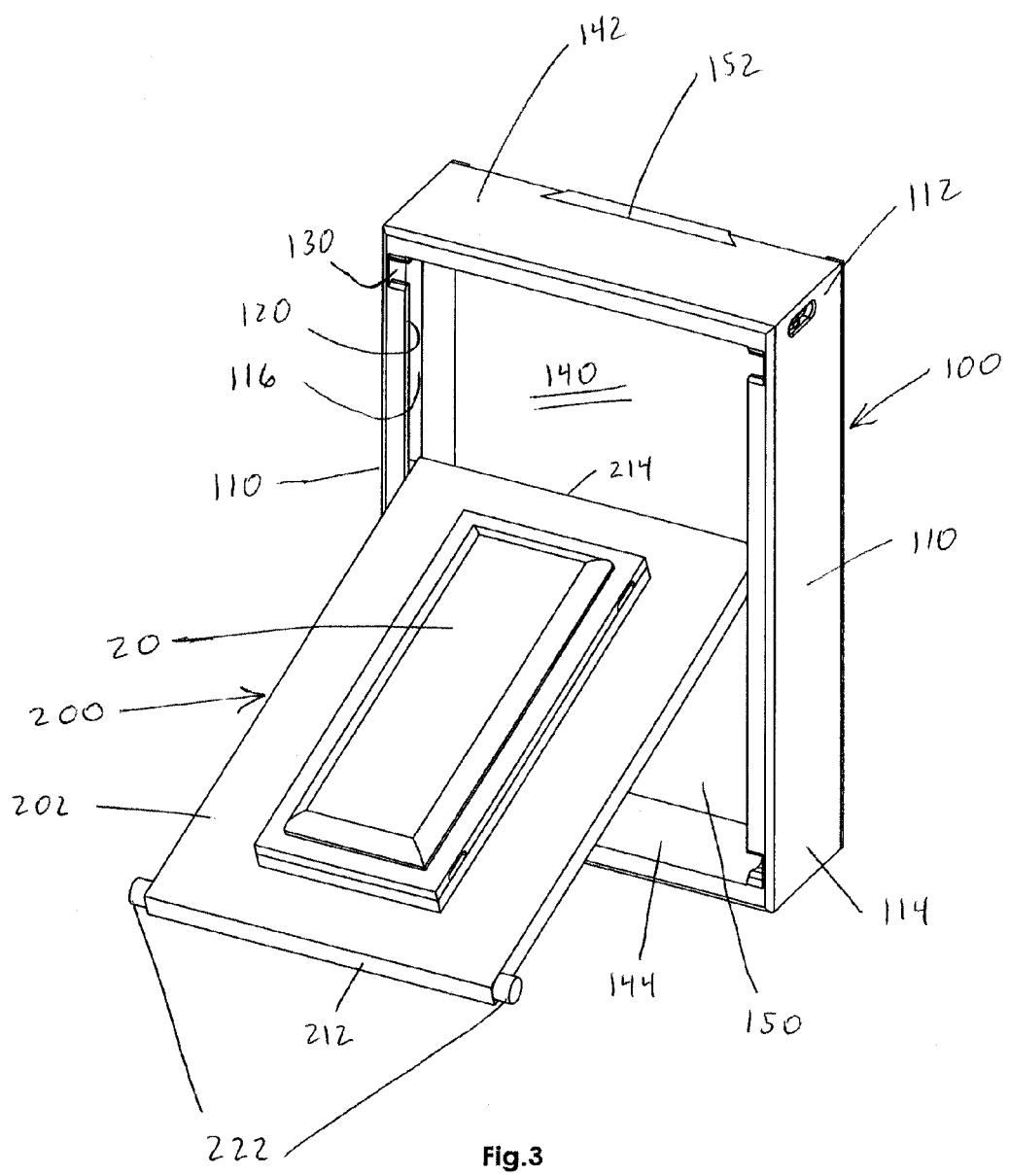
FIG. 3 is a perspective view of the dispensing apparatus, as in FIG. 1a, with a display panel shown at an intermediate position between two predetermined configurations.
Figure 5A:
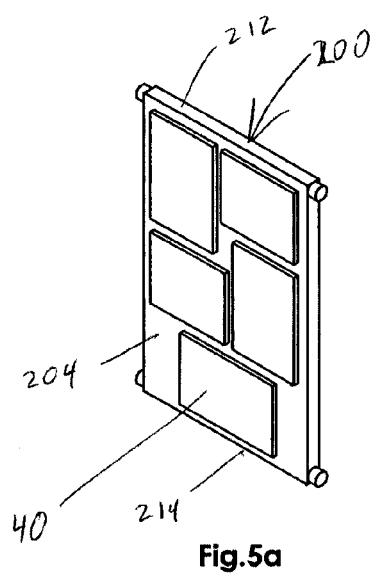
FIG. 5a is a perspective view of the display panel showing picture frames coupled to a front surface of the display panel.
Figure 5B:
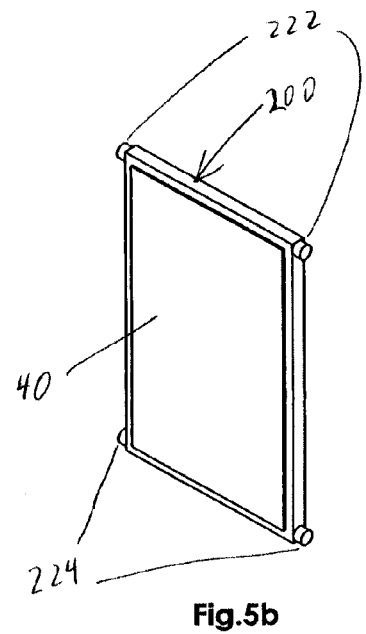
FIG. 5b is a perspective view of the display panel showing a minor coupled to the front surface of the display panel.
Figure 5C:
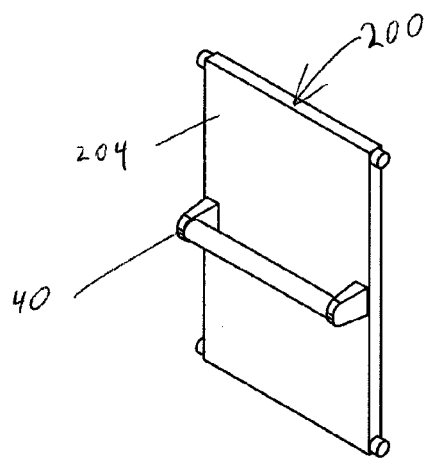
FIG. 5c is a perspective view of the display panel showing a towel bar coupled to the front surface of the display panel.
Figure 5D:
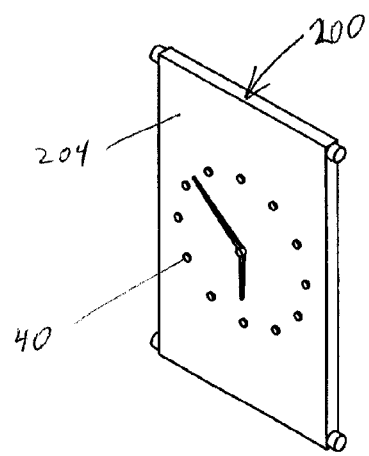
FIG. 5d is a perspective view of the display panel showing elements of a clock coupled to the front surface of the display panel.
Figure 6A:
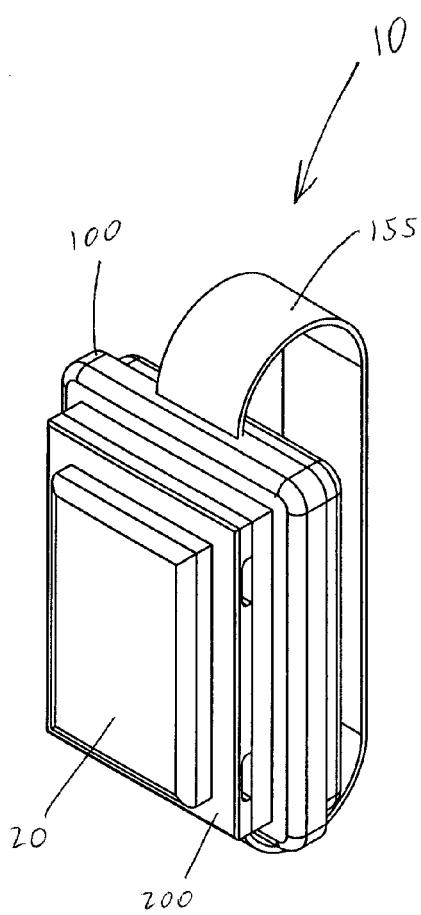
FIG. 6a is a perspective view of a dispensing apparatus according to another embodiment of the present invention.
Figure 6B:
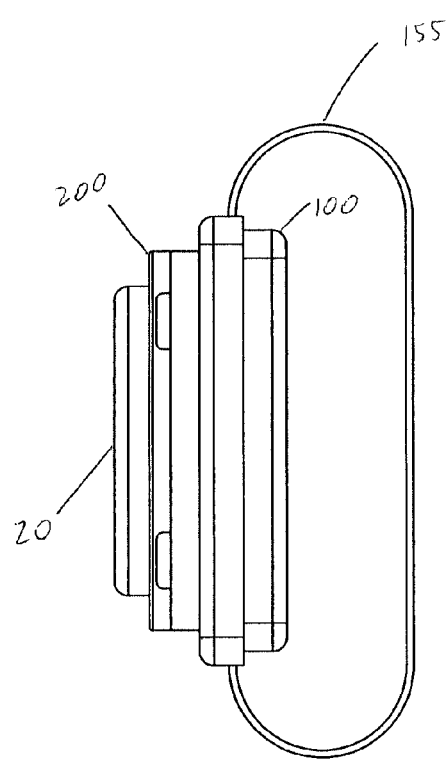

As shown in FIG. 3, the display panel 200 may be selectively movable from the first configuration to the second configuration without decoupling the display panel 200 from the display housing 100. In the preferred embodiment, the display panel 200 includes a first end 212 and a second end 214. The first end 212 includes a first pair of opposing bosses 222 extending outwardly from the first end 212 of the display panel 200. The second end 214 includes a second pair of opposing bosses 224 extending outwardly from the second end 214 of the display panel 200. Respective first and second pairs of bosses 222, 224 include configurations that are complementary to the configuration of the channels 120 and the slots 130 such that the display panel 200 is selectively and slidably movable between the first configuration and the second configuration without decoupling the display panel 200 from the display housing 100. In one embodiment, the respective first or second pair of bosses 222, 224 may be retractable.

In another embodiment, the respective first and second pairs of opposing bosses 222, 224 may each include just one boss.

Returning to the slots 130 of the preferred embodiment, each slot 130 may be configured to selectively allow a respective boss 222, 224 to enter and exit the respective channel 120. Additionally, as shown in FIG. 1c, a retention spring 132 may be situated in each slot. Each retention spring 132 may be configured to exert a predetermined force against each respective boss 222, 224 sufficient to retain each respective boss 222, 224 within each respective slot 130.

The dispensing apparatus 10 may also include a wall mounting member 154. The wall mounting member 154 may define wall mounting apertures 156 suitable to accommodate fasteners capable of installing the wall mounting member 154 to a wall. The back panel 140 of the display housing 100 may define a wall mounting channel 152 configured to selectively and receive the wall mounting member 154 (FIG. 3). This configuration may be a tongue and groove arrangement such that the display housing 100 is selectively and slidably movable along the wall mounting member 154 to a user selected height.

The display housing 100 includes an adjustment assembly 160 coupled to the display housing 100 and configured to selectively secure and release the display housing 100 from the wall mounting member 154. The adjustment assembly may include a pin 162 and a spring 164 that is biased to urge the pin 162 towards the wall mounting member 154. The wall mounting member 154 may define a plurality of spaced apart holes 156 configured to receive the pin 162 when the display housing 100 is located at various positions relative to the wall mounting member 154. The adjustment assembly 160 may include a lever 166 operatively coupled to the pin 162 and configured to selectively retract the pin 162 away from the wall mounting member 154 when actuated, releasing the display housing 100 to move slidably relative to the wall mounting member 154. In this manner, the display housing 100 may be vertically positioned at a selected height as desired by a user. When properly oriented, a person may rub his or her back against the dispensing device 20 and, as a result, apply lotion or medication to his back.

In an alternative embodiment, the dispensing apparatus 10 may include a mounting strap 155. The mounting strap 155 may be selectively coupled to the display housing 100 and may be used to operatively couple the display housing 100 to a rigid support structure, such as the back of a chair.

In use, the display housing 100 may be mounted on a wall. It should be appreciated that the display housing 100 may be hung on any wall in a residence—even a living room, office, kitchen, or bedroom—in that a neutral article such as a clock is displayed when the dispenser device 100 is not in use and, therefore, concealed as described above. The display panel 200 may be slidably moved between configurations where the dispensing device 100 is alternately used or concealed as described above. Further, the entire display housing 100 may be vertically adjusted such that the dispenser device 100 may be used by persons of different heights.

It is understood that while certain forms of this invention have been illustrated and described, it is not limited thereto except insofar as such limitations are included in the following claims and allowable functional equivalents thereof.

The invention claimed is:

1. A dispensing apparatus, comprising:
a display panel having a back surface;
a dispensing device coupled to said back surface of said display panel; and
a display housing;
wherein:

said display panel is selectively coupled to said display housing so as to define a void between said display panel and said display housing when coupled thereto;

said display panel is selectively located at a first configuration in which said dispensing device is situated within said void and a second configuration in which said dispensing device is situated outside said void;

wherein:

said display housing includes a pair of opposed upstanding side panels each having upper and lower ends, each side panel having an inner surface defining a channel extending substantially between respective upper and lower ends; and said display panel includes first and second ends with a first pair of opposing bosses extending outwardly from opposed sides of said first end and a second pair of opposing bosses extending outwardly from opposed sides of said second end;

said first pair of bosses and said second pair of bosses include a configuration complementary to a configuration of said channels and are selectively situated in said channel such that said display panel is selectively and slidably movable between said first configuration and said second configuration without decoupling said display panel from said display housing.

2. The dispensing apparatus of claim 1, wherein said dispensing device is a medicament applicator pad configured to selectively dispense a medicament.

3. The dispensing apparatus of claim 1, wherein said dispensing device is removably coupled to said back surface of said display panel.

4. The dispensing apparatus of claim 1, further comprising an article of manufacture coupled to a front surface of said display panel, wherein:

said article of manufacture is located outside of said void when said display panel is at said first configuration; and said article of manufacture is located within said void when said display panel is at said second configuration.

5. The dispensing apparatus of claim 4, wherein said article of manufacture is one of a clock, a picture frame, a mirror, or a towel bar.

6. The dispensing apparatus of claim 1, wherein said display panel has a generally planar configuration.

7. The dispensing apparatus of claim 1, wherein said display panel is selectively movable from said first configuration to said second configuration without decoupling said display panel from said display housing.

8. The dispensing apparatus of claim 1, further comprising opposed slots located adjacent to respective upper and lower ends of respective side panels and in communication with said channels, wherein the respective slots are configured to allow the respective bosses to enter and exit respective channels completely.

9. The dispensing apparatus of claim 8, further comprising a retention spring positioned adjacent to each respective slot, wherein each retention spring is configured to exert a force against said each respective boss sufficient to retain said each respective boss within its respective slot.

10. The dispensing apparatus of claim 1, wherein said display housing includes a back panel extending between respective side panels and respective upper and lower panels so as to define an interior area.

11. The dispensing apparatus of claim 10, further comprising a wall mounting member selectively coupled to said display housing.

12. The dispensing apparatus of claim 11, wherein said back panel of said display housing defines a wall mounting channel configured to couple to said wall mounting member in a tongue and groove arrangement such that said display housing is selectively and slidably movable along said wall mounting member.

13. The dispensing apparatus of claim 12, wherein said display housing includes an adjustment assembly coupled to said display housing and configured to selectively secure and release said display housing from said wall mounting member.

14. The dispensing apparatus of claim 13, wherein:

said adjustment assembly includes a pin that is spring biased to urge said pin toward said wall mounting member; and said wall mounting member defines a plurality of spaced apart holes configured to receive said pin when said display housing is located at various positions relative to said wall mounting member.

15. The dispensing apparatus of claim 14, wherein said adjustment assembly includes a lever operatively coupled to said pin and configured to selectively retract said pin away from said wall mounting member when actuated, whereby to release said display housing to move slidably relative to said wall mounting member.

16. The dispensing apparatus of claim 1, further comprising a mounting strap selectively coupled to said display housing and configured to operatively couple said display housing to a rigid support structure.

* * * * *